United States Patent [19]
Wardle et al.

[11] Patent Number: 5,415,653
[45] Date of Patent: May 16, 1995

[54] OPTICAL CATHETER WITH STRANDED FIBERS

[75] Inventors: John L. Wardle, San Clemente; Tsvi Goldenberg, Irvine, both of Calif.

[73] Assignee: Advanced Interventional Systems, Inc., Irvine, Calif.

[21] Appl. No.: 124,383

[22] Filed: Sep. 20, 1993

Related U.S. Application Data

[63] Continuation of Ser. No. 937,065, Aug. 26, 1992, abandoned.

[51] Int. Cl.6 .............................................. A61B 17/36
[52] U.S. Cl. .......................................... 606/7; 606/15
[58] Field of Search ............................... 606/7, 13–16; 607/88, 89; 385/103, 104; 604/282, 21, 22

[56] References Cited

U.S. PATENT DOCUMENTS 3,498,286  9/1966  Polanyi et al. .
4,681,104  7/1987  Edelman .
4,690,175  9/1987  Ouchi et al. ........................ 604/282
4,969,709  11/1990 Sogawa et al. ......................... 128/4
5,147,317  9/1992  Shank et al. .

Primary Examiner—Peter A. Aschenbrenner
Assistant Examiner—Michael Peffley
Attorney, Agent, or Firm—Richard L. Myers

[57] ABSTRACT

A catheter having an axis extending between a proximal end and an opposing distal end includes a plurality of optical fibers arranged to spiral in a first direction to form a circumferential layer around the axis. Rotation of the catheter in the first direction tends to expand the layer while rotation of the catheter in a second opposite direction tends to contract the circumferential layer. An outer jacket limits the expansion of the circumferential layer while an inner core limits the contraction of the circumferential layer to increase torquability of the catheter. The stranded fibers equalize bending stresses to maintain a circular cross-sectional configuration, increase flexibility and a reduced diameter for the catheter.

42 Claims, 5 Drawing Sheets

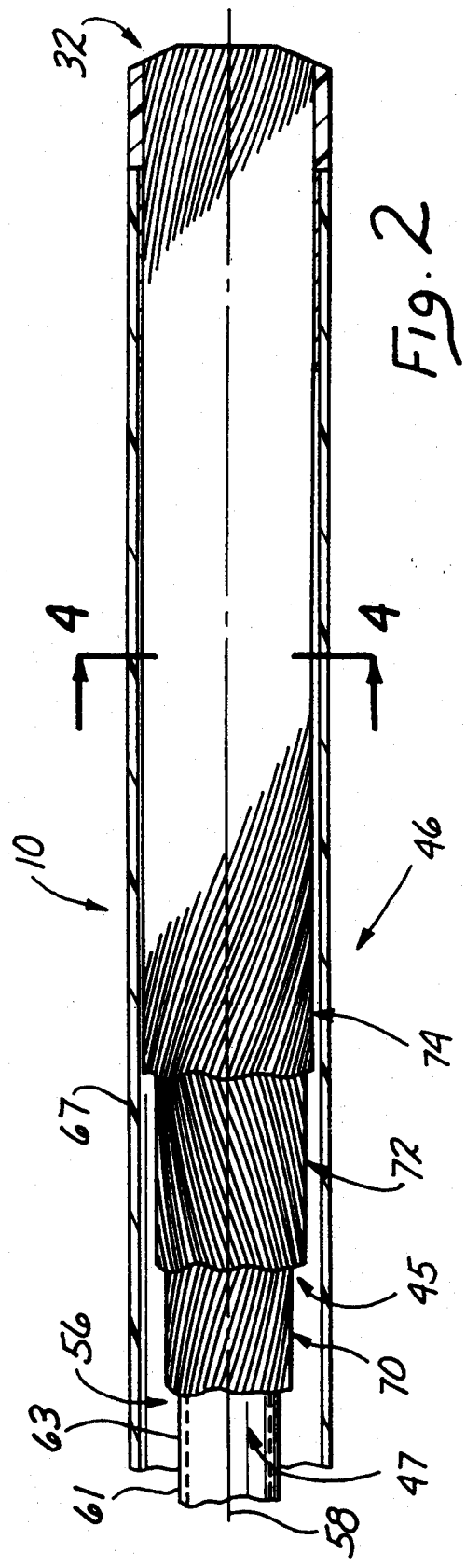
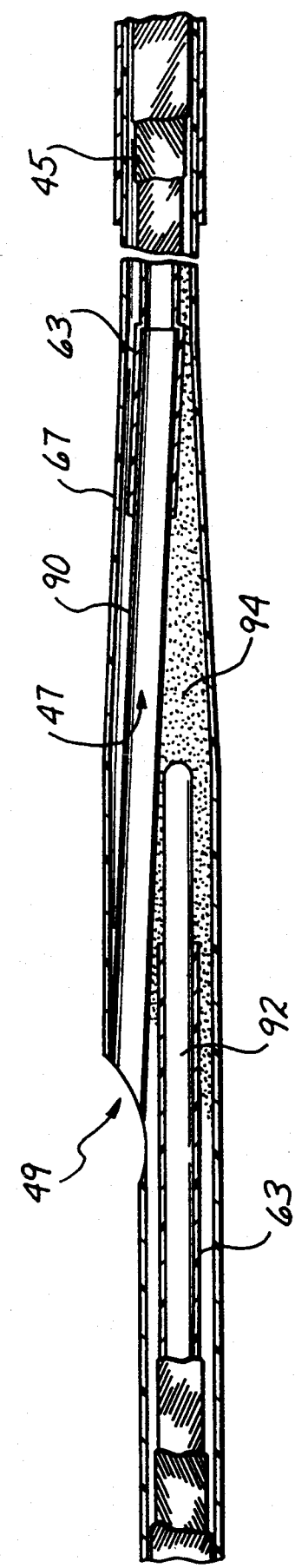

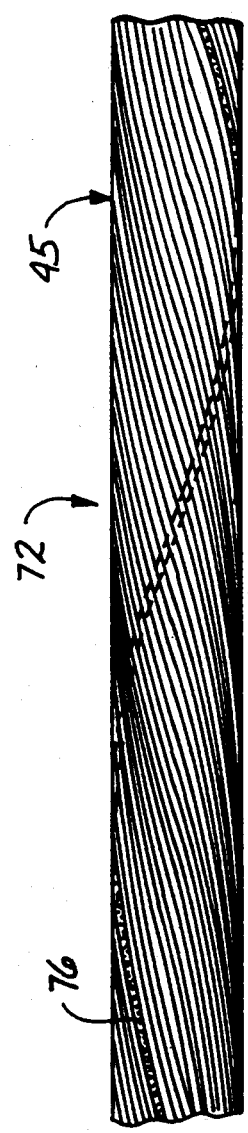
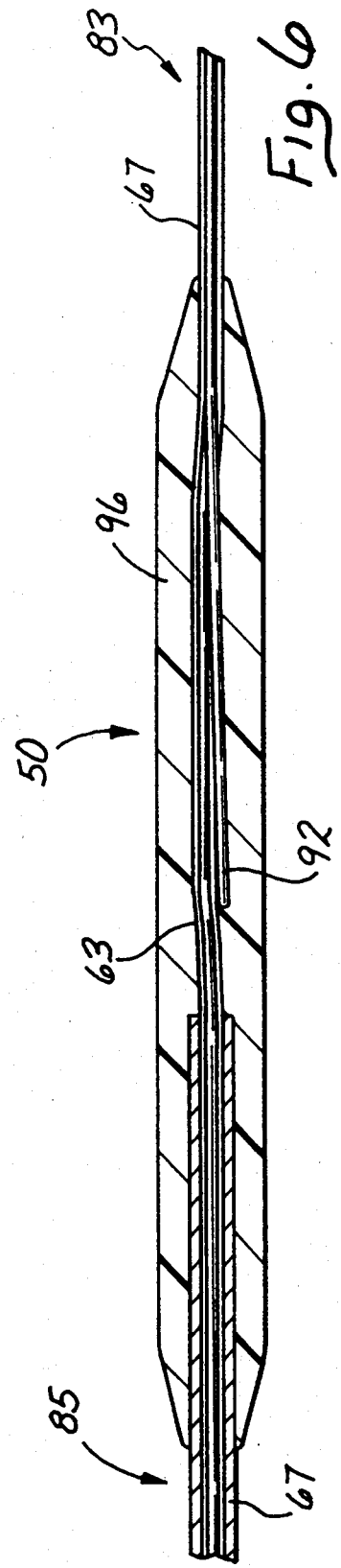
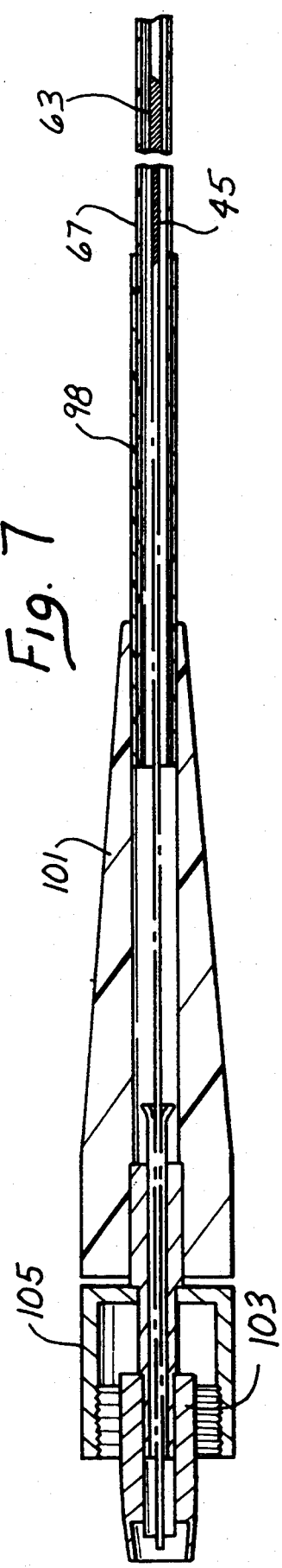

OPTICAL CATHETER WITH STRANDED FIBERS

This application is a continuation of application Ser. No. 07/937,065, filed Aug. 26, 1992, now abandoned and also entitled "OPTICAL CATHETER WITH STRANDED FIBERS".

BACKGROUND OF THE INVENTION

1. Field of the Invention

This invention relates generally to fiberoptic catheters and more specifically to laser catheters such as those used in angioplasty.

2. Background of the Invention

A surgical procedure commonly referred to as coronary angioplasty is well known in the art and is a noninvasive technique which addresses problems associated with the blockage and sometimes occlusion of coronary arteries. In this procedure, a guide catheter is typically introduced into the femoral artery in the leg and directed upwardly through the aortic arch into either the left coronary artery or the right coronary artery.

A very small guidewire is typically introduced through the guide catheter and carefully directed through the smaller coronary arteries up to and typically across the lesion of interest. An operative catheter is introduced over the guidewire and interiorly of the guide catheter until its distal end is brought into proximity to the lesion. The next step in the surgical procedure depends on the nature of the operative catheter. Balloon catheters have been used to compress the plaque, but more recently, laser catheters have been used to ablate the plaque material to increase the patency of the artery.

Laser catheters rely upon optical fibers to transmit laser energy from the proximal end of the catheter to the distal end of the catheter. In the past this transmission has taken place through a fiberoptic which may comprise a single fiber or a bundle including many small fibers which are arranged in a generally parallel configuration.

Although the laser catheter relies heavily on the guide catheter and the guidewire for manipulation, it nevertheless must have its own flexibility in order to negotiate the various bends and curves which define a typically torturous path to the lesion. It is the bending of the optical fibers that has presented particular problems for these laser catheters.

In the past, the parallel fibers have typically been housed in a catheter jacket. When the catheter is bent, the parallel fibers have unequal bending paths. With an outer jacket closely spaced to the fiber bundle, the catheter would have a very high resistance to bending due to the restriction of movement. It has been found that this resistance can be decreased by providing some space between the fiber bundle and the catheter jacket. This space increases the ability of the fibers to move relative to each other as required when the catheter is bent. Unfortunately, in an environment wherein catheter diameter is particularly critical, any provision of space to accommodate bending is provided only at a great sacrifice to catheter size.

These catheters of the past have typically been constructed by inserting the delicate fibers into one end of the catheter jacket. Attempts to coextrude the fibers and jacket have not provided the requisite space to facilitate bending of the catheter.

The bending of parallel fibers has other undesirable mechanical consequences. The fibers on the interior edge of the curve are placed in compression and tend to move away from the jacket toward the axis of the catheter. In contradistinction, the fibers on the outside of the curve are placed in tension, but they also tend to move away from the jacket toward the axis of the catheter. This results in a flattening of the catheter along the curve. While the flattening produces a reduction in the catheter width in the plane of the curve, this reduction in width is necessarily accompanied by a corresponding expansion of the catheter width in a direction perpendicular to the plane of the curve. Thus a catheter that has a specific diameter tends to increase in size when it is bent or curved. In some cases this increase is sufficient to cause the laser catheter to bind on the inner surface of the guide catheter.

In all cases, this expansion problem results in increased resistance to movement of the laser catheter within the guide catheter. This cannot be tolerated in a surgical procedure as delicate as angioplasty. As the surgeon moves the laser catheter through the arteries, any resistance to movement is relied on to convey information as to resistance at the distal tip not increased friction along the catheter wall. Using a longer guide catheter to reduce friction is surgically undesirable.

Another problem associated with the parallel orientation of optical fibers has been their general inability to transmit torque from the proximal end of the catheter to the distal end of the catheter. In order to add torsional rigidity to the catheter, it has been necessary to provide a large torque wire or a metallic braid along the entire length of the catheter. This of course has either increased the size of the catheter or consumed space which would otherwise be available within the catheter.

These attempts to solve the problems of the prior art have left a requirement for a fiberoptic catheter having greater flexibility and torque transmission characteristics, reduced diameter and bending stresses, without any sacrifice to size or interior space.

SUMMARY OF THE INVENTION

In accordance with the present invention, a fiberoptic catheter is provided with increased flexure characteristics, an even distribution of bending stresses in the fibers, and a smaller overall diameter for the catheter. Importantly, these features can be achieved without the addition of any further components or the sacrifices of any space within the catheter. These characteristics, which make the fiberoptic catheter of primary interest as a laser catheter, are particularly appreciated in an angioplasty procedure.

The catheter of the present invention includes a multiplicity of optical fibers which are disposed in an ordered rather than random arrangement around a core. The fibers are typically wound in a spiral or helical configuration to form at least one circumferential or cylindrical layer around the axis of the catheter. This spiral configuration greatly increases the torquability of this catheter. As the catheter is torqued in the direction of the spiral, the fibers in this circumferential layer tend to expand outwardly. Means is provided around the fibers to limit this expansion. Alternatively, if the catheter is torqued in the opposite direction, the circumferential layer tends to contract. Means is provided interiorly of the circumferential layer to inhibit this contraction. Thus the catheter is provided with significant torque characteristics by merely orienting the existing components, namely the optical fibers, in a particular pattern.

Both of the limiting means can be formed from additional circumferential layers of the optical fibers which are wound in alternating directions.

This configuration of stranded fibers is of particular interest where the catheter is curved or bent. It is first noted that with the stranded configuration, all of the fibers experience substantially the same bending stresses. Unlike a parallel fiber matrix wherein a bent fiber is located at a set location throughout its curve, a fiber in a stranded configuration continuously changes its location from the inner radius of the curve to the outer radius of the curve. Its shortened path on the inner radius is equal to its lengthened path on the outer radius. The net result of this stranded configuration is a self-compensating, lengthening and shortening of the fibers path around the curve resulting in an unchanged overall length for the fiber. Since the fibers individually compensate for their tendency to compress on the inner radius of the curve and expand on the outer radius of the curve, the cross-section of the catheter remains substantially circular and avoids any increase in friction between the laser catheter and the guide catheter at the curve. This greatly increases the tactile feedback of the catheter during catheter insertion.

Although the spiral fibers may require a greater diameter for the bundle, there is no requirement for space between the bundle and the jacket of the catheter. This has two beneficial results. First, the jacket can be laid directly upon the fibers thereby producing an overall smaller catheter diameter. Second, without the requirement for space between the fiber bundle and the jacket, the jacket can be co-extruded directly onto the fiber bundle. This construction lends itself to an on-line continuous process.

In one aspect of the invention, a fiberoptic catheter having an axis extending between a proximal end and a distal end comprises a plurality of optical fibers arranged in a spiral configuration around the axis to form a circumferential layer. The fibers are arranged to spiral in a first direction so that rotation of the catheter in the first direction tends to expand the circumferential layer while rotation of the catheter in a second direction opposite to the first direction tends to contract the circumferential layer. First means is disposed outwardly of the circumferential layer for limiting the expansion when the catheter is rotated in the first direction, and second means is disposed inwardly of the circumferential layer to limit the contraction when the catheter is rotated in the second direction.

In another aspect of the invention, a method provides for increasing the torque characteristics of a catheter having an axis extending between a proximal end and an opposing distal end. The method includes steps for providing a plurality of fibers and wrapping the fibers around the axis to form a single, generally cylindrical, layer having properties for expanding radially when the catheter is twisted in a first direction and properties for contracting radially when the catheter is twisted in a second direction. By providing a cylindrical surface inwardly of the fiber layer an interference fit is created with the contracting fibers. Similarly, by providing a cylindrical surface outwardly of the fiber layer an interference fit is created with the expanding fibers.

In a further aspect of the invention, a catheter having an axis extending between a proximal end and a distal end includes a plurality of optical fibers. The catheter is bendable between a first position wherein the axis of the catheter is generally straight and the catheter in radial cross-section has a first shape, and a second position wherein the axis of the catheter forms a curve and the catheter in radial cross-section has a second shape. The optical fibers in this aspect are arranged in a pattern so that the second shape is maintained in a configuration which is substantially similar to the first shape.

These and other features and advantages of the invention will be more apparent with a discussion of preferred embodiments of the concept and reference to the associated drawings.

DESCRIPTION OF THE DRAWINGS

FIG. 2 is an axial side view partially in section of a preferred embodiment of the invention;

FIG. 3 is a side view of a single layer of stranded fibers including a particular fiber;

FIG. 5 is an axial view partially in cross-section and illustrating a guide lumen exit port associated with a preferred embodiment of the invention;

FIG. 6 is an axial view partially in cross-section and illustrating a torque handle in the preferred embodiment of the invention; and FIG. 7 is an axial view partially in cross-section and illustrating a distal hub in a preferred embodiment of the invention.

DESCRIPTION OF PREFERRED EMBODIMENTS AND BEST MODE OF THE INVENTION

Figure 1:
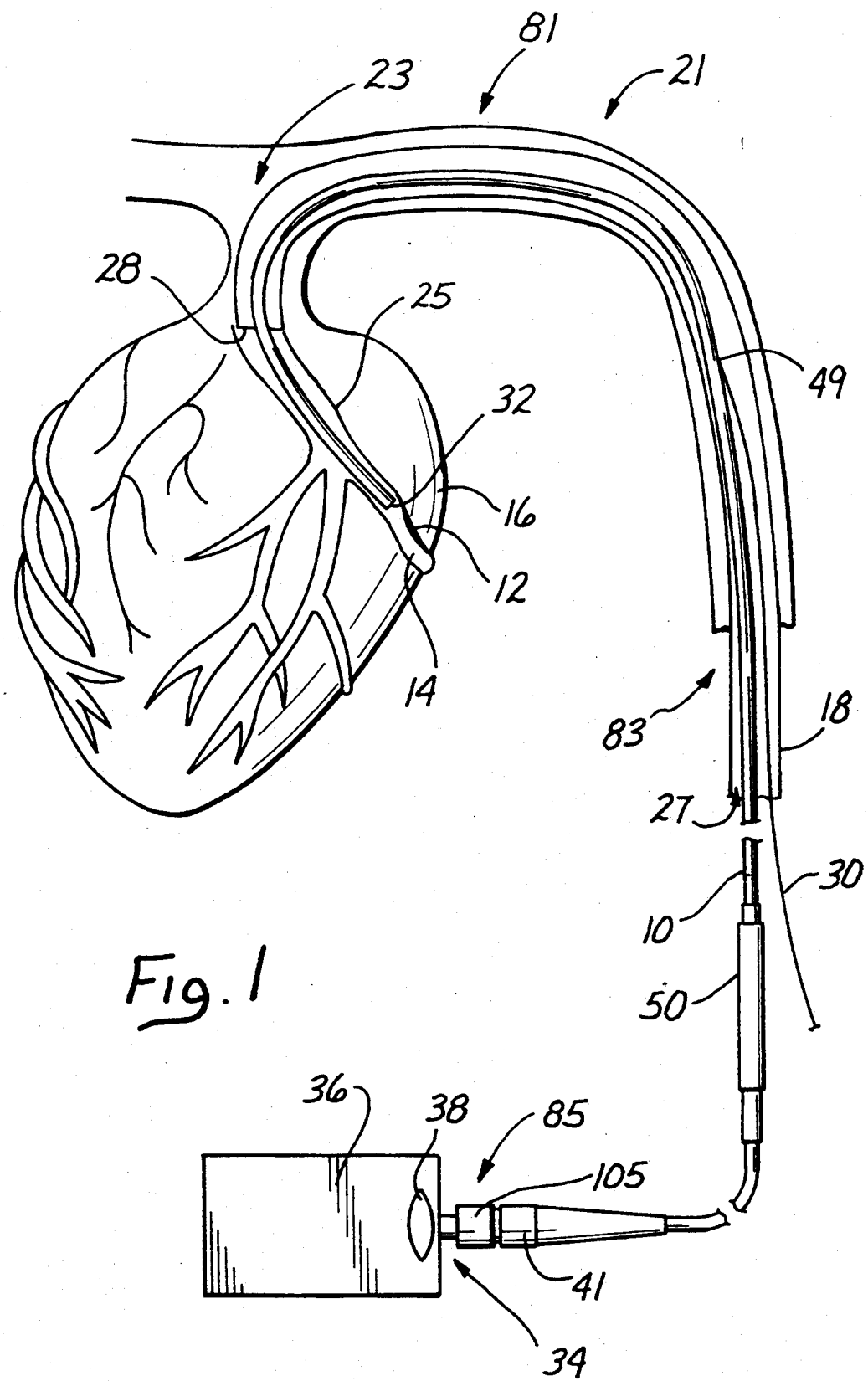
FIG. 1 is a schematic view showing a heart with coronary arteries and a laser catheter operative disposed to ablate a lesion.

A fiberoptic catheter is illustrated generally in FIG. 1 and designated by the reference numeral 10. This catheter 10 in the illustrated embodiment is a laser catheter and is operatively disposed to ablate plaque 12 in a coronary artery 14 of a heart 16. The laser catheter 10 is one of several types of catheters which can be used to address clogged arteries in a procedure commonly referred to as angioplasty. In such a procedure, an incision is initially made into an artery in the vicinity of the groin. A guide catheter 18 is moved upwardly in the artery through the aortic arch 21 and into either the right coronary artery or the left coronary artery 25, as illustrated in FIG. 1.

The guide catheter 18 has a relatively large lumen 27 defined by a inner surface. This lumen 27 extends from a proximal end of the guide catheter 18 to a distal end 28. Due to the relatively large size of the guide lumen 27, the distal end 28 of the catheter 18 is not intended to enter the narrow tributary vessels of either the right or the left coronary artery 25.

In order to reach the lesion 12, a guidewire 30 is introduced through the lumen 27 of the guide catheter 18. The guidewire 30 is moved easily through the guide catheter 18 to the distal end 27 where it is passed with increasing difficulty through the smaller coronary arteries up to and typically across the lesion 12. Both the guide catheter 18 and the guidewire 30 are provided with superior torque and deflection characteristics which enable them to be moved into these respective operative positions. When these guiding instruments are in place, they can be relied upon to guide the operative catheter, such as the laser catheter 10, along the torturous path to the lesion 12.

The catheter 10 has a distal end 32, and a proximal end 34 which is attached to a laser 36. By way of example, the laser 36 may be an Zenon Chloride Excimer laser providing a pulsed output in a frequency range of twenty to thirty Hertz. Other pulsed lasers may be equally applicable particularly with wavelengths in a preferred range between 0.2 and 12 microns. An energy coupler 38 concentrates the optical energy which is then introduced through a catheter coupling 41 into the catheter 10. Optical fibers 45 (best shown in FIG. 2) are collectively referred to as a bundle 46 and carry this optical signal through the catheter 10 to the distal end 32 where it is used to ablate the plaque 12.

In addition to the optical fibers 45, the catheter 10 includes a guide lumen 47 which is adapted to receive the guidewire 30 and guide the catheter 10 into its operative position. This guide lumen 47 extends from the distal end 32 of the catheter to an exit port 49, the purpose and location of which is described in greater detail below. With the guide catheter 18 and guidewire 30 operatively disposed, the distal end. 32 of the catheter 10 is pushed onto the proximal end of the guidewire 30 and into the guide lumen 27 of the catheter 18. The guidewire 30 remains within the catheter 10 up to the exit port 49 and then exits the catheter 10. Proximal of the exit port 49, the catheter 10 and the guidewire 30 are separated within the lumen 27 of the guide catheter 18. The catheter 10 also includes a torque handle 50 which is described in greater detail with reference to FIG. 6.

The interior regions of the catheter 10 are best illustrated in the fragmented view of FIG. 2 which includes the distal end 32. In this view, the catheter 10 is illustrated to have a core member 56 which is disposed along an axis 58. The core member 56 may be solid or tubular in configuration, but in either case is intended to provide a cylindrical outer surface 61 concentric with the axis 58. Thus the core member 56 may comprise a solid optical fiber or a tube 63 having the inner guide lumen 47. In this configuration the lumen 47 is adapted to receive the guide wire 30 from the distal end 32 to the exit port 49 for the purposes previously discussed.

Of particular interest to the present invention are the optical fibers 45 and particularly their pattern or arrangement relative to each other between the tube 63 and an outer jacket 67 of the catheter 10. As illustrated in FIG. 2, the fibers 45 can be disposed in three separate circumferential layers, namely, an inner layer 70, a middle layer 72, and an outer layer 74. In each of these layers 70-74, the fibers 45 individually and collectively form a spiral around the axis 58. Adjacent fibers can be spaced or can be disposed in the contacting, contiguous relationship illustrated.

The fibers 45 in a particular layer may be wound radially axially in the same direction and equidistant from the axis 58. With this configuration, the layers 70-74 each tend to take the shape of a cylinder. It is important to note that each of the fibers 45 in a particular one of the layers 70-74 follows a bending path which is generally similar in shape and length to the bending paths followed by each of the other fibers in that layer. This insures that the bending stresses for each of the fibers in the layer are substantially equal, and ultimately facilitates bending the catheter 10 along a smaller radius. Of even greater interest is the fact that a stranded catheter will have increased flexibility with respect to a non-stranded catheter having the same number of fibers and the same cross-sectional fiber area. This flexibility is particularly appreciated when the catheter is required to negotiate torturous vessel paths. Of even greater interest is the fact that a stranded catheter will have increased flexibility with respect to a non-stranded catheter offering the same number of fibers and the same cross-sectional fiber area. This flexibility is particularly appreciated when the catheter is required to negotiate torturous vessel paths.

The fibers in adjacent layers are preferably wound to spiral in opposite directions, while the fibers in alternating layers are preferably wound to spiral in the same direction. Thus, it can be seen that the fibers of the middle layer 72 are wound in a left hand spiral, in other words, counter-clockwise to the axis 58. In contradistinction, the fibers forming the layers 70 and 74 are wound in a right hand spiral or clockwise to the axis 58.

As used herein, the word "spiral" is best defined as a loci of points extending equidistant from the axis 58 with progressive radial and axial positions. A given one of the fibers 45 follows a path similar to that of a screw thread and consequently has a pitch as discussed in greater detail below. Winding the fibers in this spiral configuration is referred to as "stranding".

In a typical method of manufacture, the fibers 45 forming the inner layer 70 are wound or stranded On the outer surface 61 of the tube 63. Then the fibers 45 forming the middle layer 72 are wound or stranded in the opposite direction over the fibers forming the inner layer 70. Finally, the fibers forming the outer layer 74 are wound or stranded on the middle layer 72. It follows that the fiberoptic bundle 46 in this embodiment includes all of the fibers 45 and is configured in a pattern of three cylindrical layers 70-74 which are contiguous and coaxial with the core member 56. The fiberoptic bundle 46 may include a single layer or multiple layers, in the latter case adjacent layers are preferably wound or stranded in opposite directions.

In the various embodiments of the invention, the fibers 45 can have different diameters in different layers 70-74 and even within the same layer. The bundle of fibers 46 may also include strands or fibers which are not optical. For example, electrical wires and radiopaque fibers can be included among the strands. One or more electrical fibers can be included to transmit electrical signals between the distal end and the proximal end 34. Since the location of each of the fibers is carefully controlled in the stranding process, these electrical fibers could be placed so that no insulation is required to maintain their electrical isolation. For example, multiple electrical fibers could be included in the middle layer 72 and would be isolated from each other throughout the length of the catheter 10.

In the case of radiopaque fibers, these could assist the surgeon in locating the catheter, particularly the distal end 32, in the desired axial or angular orientation. An example of a layer, such as the middle layer 72 containing a single electrical or radiopaque fiber 76 is illustrated in FIG. 3.

A significant advantage associated with stranding the fibers 45 is based on the superior torque capability which this configuration provides for the catheter 10. In the past, fibers have been disposed in a parallel configuration so that they provided no assistance in torquing the catheter 10. Other structures such as torque wires and metallic braids have been required in the catheters of the past to accommodate the need for torque control.

Torquing generally refers to the ability of a catheter to be twisted radially at the proximal end and to produce a corresponding radial twist at the distal end of the catheter. When the fibers 45 are spiraled as illustrated in FIG. 2, a radial torque in the direction of the spiral, such as the left hand direction for the middle layer 72, will place the fibers 45 in compression and cause them to expand outwardly. In contradistinction, a radial torque in the right hand direction will place the fibers 45 of the middle layer 72 in compression and cause them to contract radially inwardly. The resulting effect is that the layer 72 expands radially outwardly in response to a right-hand torque and contracts radially inwardly in response to a left-hand torque. The opposite effect occurs for the layers 70 and 74 since the fibers in these layers are wound in the opposite direction.

Torque control is enhanced when means is provided interiorly of the layer, such as the middle layer 72, to limit the contraction and exteriorly of the layer to limit the expansion. In the case of the layer 70 illustrated in FIG. 2, the tube 63 has a fixed outer diameter and therefore limits the contraction of the layer 70. The layer 72 is disposed outwardly of the layer 70 and therefore limits its expansion.

With respect to the middle layer 72, the inner layer 70 limits its contraction while the outer layer 74 limits its expansion. With respect to the outer layer 74, the middle layer 72 limits its contraction while the jacket 67 of the catheter limits its expansion. Thus, the means for either limiting the expansion or contraction of a given layer can be a solid object having a fixed diameter such as the outer surface of the tube 63 or the inner surface of the jacket 67. Alternatively, these limiting means may include adjacent layers of the fibers 45.

When the limiting means include adjacent layers of the fibers 45, an additional advantage accrues to the structure particularly if the fibers of the adjacent layer are wound in the opposite direction. In such a case, torquing in a single direction will cause one layer to expand while the adjacent layer contracts. For example, torquing the catheter 10 in a clockwise direction will cause the middle layer 72 to contract while the inner layer 70 is caused to expand. In this case, the inner layer 70 provides the limiting means, however its outer surface is moving rather than stationery so that the interference fit between the two layers 70 and 72 occurs more rapidly. If the catheter 10 is torqued in a clockwise direction, the middle layer 72 tends to expand and creating an interference fit with the outer layer 74 which tends to contract. Thus an embodiment including three layers such as the layers 70–74, provides a rapid interference fit between at least two of the layers regardless of the direction of the torque.

Figure 4:
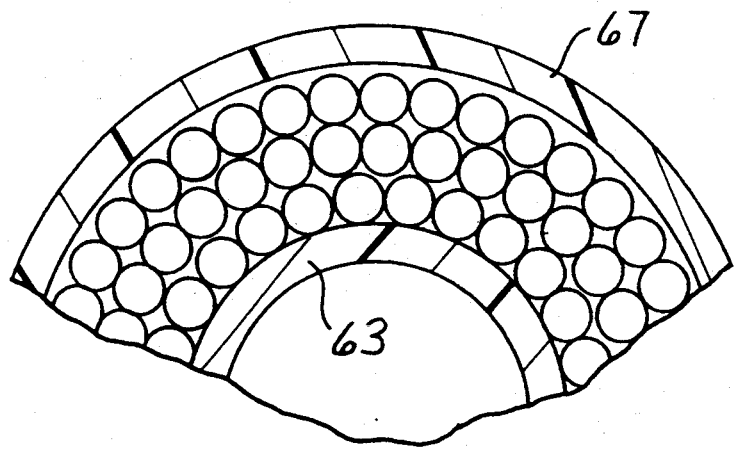
FIG. 4 is a radial cross-section view taken along lines 4—4 of FIG. 2 and illustrating three layers of fiber in a normally unstressed state.
Figure 4A:
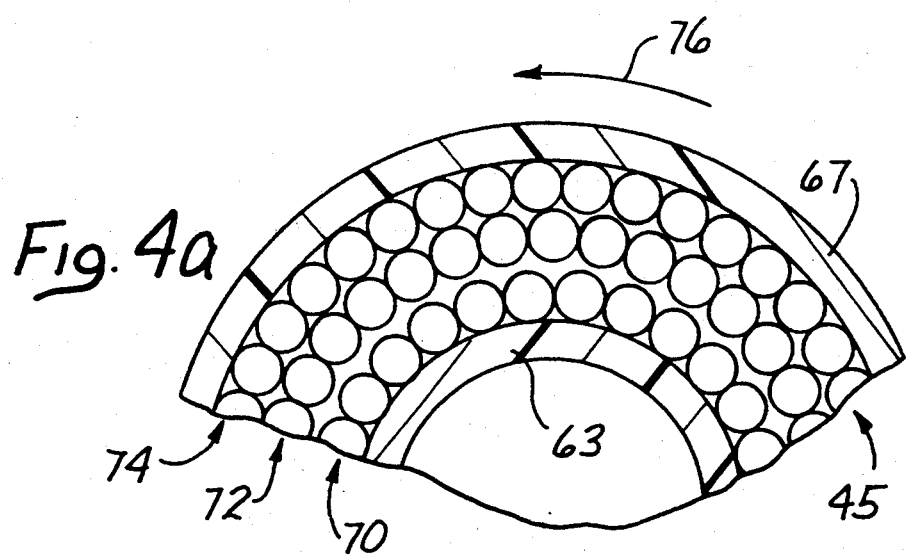
FIG. 4a is a radial cross-section view taken along lines 4—4 of FIG. 2 and illustrating a middle layer and an outer layer of fibers in an interference fit.
Figure 4B:
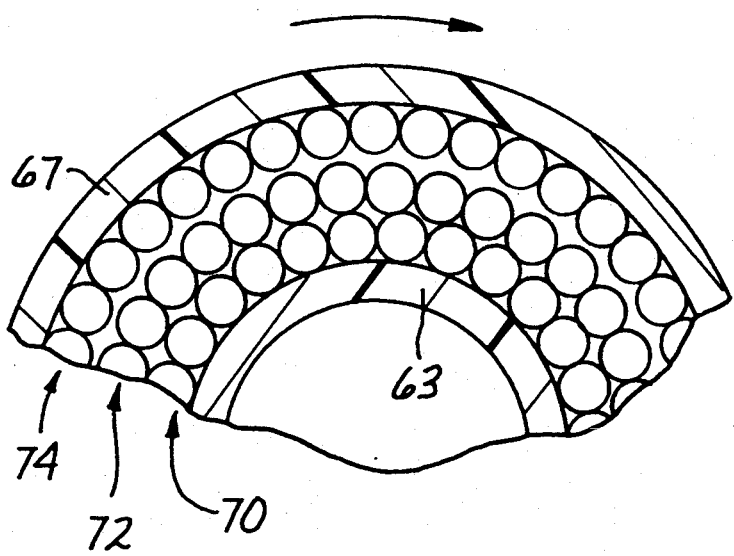
FIG. 4b is a radial cross-section view taken along lines 4—4 of FIG. 2 and illustrating a middle and inner layer in an interference fit.

These interference fits can be better understood with reference to the various cross-sections of FIGS. 4, 4a and 4b. In FIG. 4, the fibers 45 are shown to be contiguous in the same layer and also contiguous in adjacent layers. This is the normal, non-torqued configuration. However, when the catheter 10 is torqued in a counterclockwise direction (the direction arrow 76 in FIG. 4a), the fibers forming the middle layer 72 expand radially outwardly while the fibers forming the inner layer 70 and the outer layer 74 tend to contract radially inwardly. Thus as illustrated in FIG. 4a, an interference fit exists between fibers in the adjacent layers 72 and 74. An interference fit also exists between the inner layer 70 and the tube 63.

When the catheter 10 is torqued in the opposite direction, such as the counter clockwise direction illustrated by arrow 78 in FIG. 3b, the opposite circumstances occur. The fibers 45 in the middle layer 72 contract while the fibers forming the layers 70 and 74 expand. Thus an interference fit occurs between the layers 70 and 72. An interference fit also exists between the fibers in the layers 74 and the jacket 67.

It will be appreciated that this concept is not limited to only three layer embodiment, however. Certainly more than three layers would enhance the torque characteristics of the catheter 10. But even a single layer which is wound on a fixed cylindrical surface, such as the surface 61, and which is outwardly limited by a fixed surface, such as the inner surface of the jacket 67, would benefit from the concept of this invention.

It will also be apparent that even when adjacent layers are wound in the same direction, a difference in the pitch of the winding for adjacent layers could result in an interference fit. Thus, the word "direction" is used not only to refer to radially opposite orientations, but also to refer to radially similar orientations but different pitches.

The pitch of the fiber 45 describes the axial length traveled by the spiral as it completes one full revolution around the axis. If the fibers in a given layer, such as the layer 70, are maintained in a contiguous relationship, all of the fibers have the same pitch. However, this pitch can be changed in any axial section of the catheter 10 in order to provide different torque, flexibility, and optical transmission characteristics. It is generally appreciated that a tighter pitch is equivalent to greater flexibility and torque transmission, but reduced optical transmission characteristics. However, a tighter pitch necessarily requires a greater length for the fibers which equates to increased transmission losses along the fiber. It will be appreciated that the pitch of the fibers can vary between different layers 70–74 and can also vary within a particular layer. Such is the case in another preferred embodiment of the catheter 10.

Such a catheter is illustrated in FIG. 1 to include three sections, namely a distal section 81 a middle section 83 and a proximal section 85. The distal section 81 extends from the distal end 32 to the vicinity of the exit port 49. The middle section extends from the exit port 49 through the torque handle 50 and into proximity to the coupler 41. The proximal section 85 extends through the catheter coupling 41. In each of these sections 81–85, the fibers 45 are wound in a different configuration to achieve different results. In the distal section 81, each of fibers 45 in each of the layers 70–74 are wound at the same pitch, albeit different directions as previously discussed. This pitch is relatively tight in order to achieve the advantages of increased flexibility and torque transmission.

In the middle section 83, the pitch is the same for each of the three layers 70–74, but that pitch is longer than the pitch in the distal section 81. The longer pitch in the middle section 83 covers the greater distance and therefore takes advantage of reduced transmission losses. This advantage is achieved with some sacrifice to torque and flexibility. In the proximal section 85, torque and flexibility are of less concern and the fibers are permitted to maintain a generally parallel configuration through the coupler 41. The fibers are parallel in the proximal section 85 in order to accommodate the direct input of laser energy to the fibers. By providing a better coupling match with the laser 36 the catheter 10 provides for a more efficient launch of the laser light.

In this particular embodiment, the catheter diameter is about 0.050 inches. The core member 61 comprises a teflon tube having an inside diameter of 0.020 inches and an outside diameter of 0.026 inches. The fibers 45 are each formed with a core of 60 micron fused silica glass and are ninety-nine in number. These fibers 45 are stranded in the three layers 70–74 previously discussed with alternating directions of spiral. In a given section, the pitch of the fibers 45 is the same for the three layers, but this pitch varies in the three sections 81–85. In the distal section 81, the pitch is 0.38 inches and extends for approximately fifteen inches from the distal end 32. In the middle section 83 the pitch is approximately 0.76 inches and extends for an additional 130 inches. In the proximal section 85 the fibers are parallel for a distance of approximately fifteen inches.

The concept of stranding also provides for a coherent bundle of the fibers 45. In other words, the fiber 45 do not have random positions but rather given locations within each layer so the proximal end of the fiber can be matched with the distal end of the fiber. This is of particular interest when the optical fibers are conveying a picture from the distal end 32 to the proximal end 34 of the catheter 10, or when the catheter is used for selective ablation at the distal tip.

The exit port 49 as illustrated in the enlarged cross-sectional view of FIG. 5. In the vicinity of this port 49, the core tube 63 is severed and a short length of tubing 90 is inserted through the jacket 67 and coupled to the distal end of the severed tube 63. Thus the tube 63 and the tube 90 combine to form the guide lumen 65 which extends from the distal end 32 to the exit port 49.

It can be appreciated that the addition of the tubing 90 tends to stiffen the catheter 10 in the vicinity of the exit port 49. For this reason it is desirable that the port 49 be located at a distance from the distal end 32 which is sufficient to insure that the exit port 49 does not enter the aortic arch 21. Such a construction insures that this stiffer portion of the catheter 10 is not required to bend as the catheter is inserted for ultimate placement in the coronary artery 12. Thus the exit port 49 will typically be spaced from the distal end 32 a distance which is less than fifty centimeters but greater than 25 centimeters. In a preferred embodiment, the exit port 49 is located 25 centimeters from the distal tip 32.

Proximally of the port 49, the core tube 63 in the middle section 83 does not participate in the function of the guide lumen 65. However, in this middle section, advantage can be taken of the vacant tube 63, to increase the torque transmission characteristics over the section 83 where the longer stranding pitch was elected at some sacrifice to torque. Thus, in this section 83, the tube 63 can be filled with a torque wire 92. It is generally advisable to have this wire 92 extend beyond the distal end of the severed tube 63 in order that it can be firmly imbedded in epoxy 94. This construction of the catheter 10 in the vicinity of the exit port 49 is accomplished without breaking any of the fibers 45. In other words, each of the fibers 45 extends continuously from the distal section 81 and into the middle section 83.

The torque wire 92 extends proximally through the middle section 83 and terminates generally at the torque handle 50 which is best illustrated in FIG. 6. The torque handle 50 includes an elongate sleeve 96 of enlarged diameter which extends over the jacket 67 in the middle section 83, and over the enlarged jacket 67 in the proximal section 85. Within the torque (handle) 96, the torque wire 92 is removed from the core tube 63 so that it tends to move off axis where it can be firmly held, for example in epoxy (not shown). As an alternative to epoxy, the torque handle 96 can be molded directed over the torque wire 92 as illustrated in FIG. 6.

The proximal section 85 of the catheter 10 is best illustrated in FIG. 7. At a distance of approximately 15 inches from the proximal end 34, the core tube 63 can be terminated and the fibers 45 permitted to maintain a generally parallel relationship to achieve the advantage previously discussed. In the vicinity of the coupler 38, a strain relief sleeve 98 surrounds the catheter jacket 67 and extends into a molded rubber housing 101. The fibers 45 in their parallel relationship pass through the housing 101 and exit the catheter at a male fitting 103. A screw cap 105 is provided to attach the fitting 103 to the laser 36 as illustrated in FIG. 1.

Certainly one of the primary advantages associated with a stranded catheter is its torquability. Ablation in the absence of torque would produce only discrete holes in the plaque. The unablated material between the discrete holes would inhibit forward movement of the catheter. But ablation accompanied with axial turning or torquing of the catheter functions to fully ablate all of the material thereby facilitating forward movement of the catheter. Torquing is of even further advantage in the catheter which requires radial orientation to address a particular plaque formation.

Figure 8A:
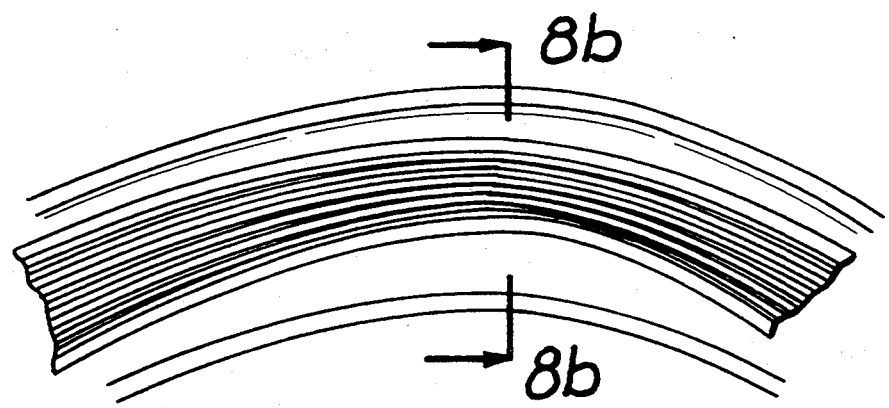
FIG. 8A is an axial cross-section view of a guide catheter and enclosed laser catheter of the prior art having parallel fibers.
Figure 8B:
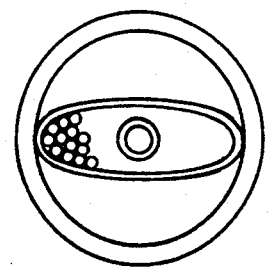
FIG. 8B is a radial cross-section view taken along lines 8B—8B of FIG. 8A.

Another of the primary advantages associated with the stranded catheter, is its ability to evenly distribute bending stresses among the fibers 45 and to maintain a generally fixed cross-sectional configuration. These features can be better understood with reference to the diagrams of FIGS. 8 and 9. In FIG. 8a, a prior art catheter 108 having a jacket 109 and parallel fibers 110, is illustrated to be bent through a section of guide tubing 112. As illustrated in the cross-section view of FIG. 8b, the parallel fibers 110 of the prior art tended to move toward the axis of the catheter 108 so that the catheter sheath 109 is compressed vertically but expanded horizontally. This expansion tends to bring the jacket 109 of the catheter 108 into frictional contact with the walls of the guide tubing 112. Unfortunately, the increased friction can be interpreted by the surgeon as being associated with cutting resistance or some blockage at the distal end of the catheter. This misinformation can greatly interfered with the delicate placement of the catheter.

Figure 9A:
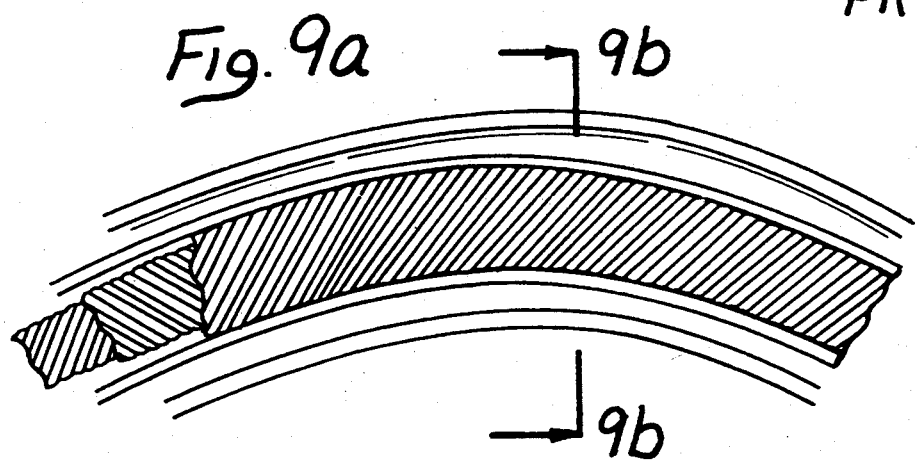
FIG. 9A is an axial cross-section view of a guide catheter and laser catheter of the present invention having stranded fibers.
Figure 9B:
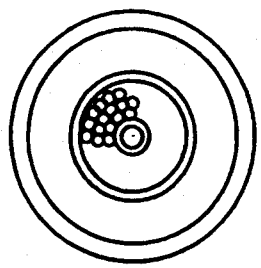
FIG. 9B is a radial cross-section view taken along lines 9B—9B of FIG. 9A.

With the catheter 10 of the present invention, illustrated in FIG. 9a, bending stresses are maintained substantially equally throughout the bundle 46 of the fibers 45. As a consequence, there is no tendency for the fibers to compress or expand in any direction. Rather, the generally Circular cross-section of the catheter 10 is maintained even through curves of small radius. The much appreciated result is that the jacket 67 of the catheter 10 does not tend to bind on the walls of the guide catheter 18, and there is no misinformation communicated to the surgeon.

The advantages associated with the catheter 10 are numerous. Relative to catheters of the prior art the catheter has increased flexure characteristics, increased torque transmission characteristics, increased tactile feedback, and all this with a reduced catheter diameter. This stranding concept not only accommodates a procedure for rapidly exchanging catheters, with a distally located exit port 49, but it also provides effective light transmission and torque characteristics without an increase in size which has heretofore been necessary to accommodate a torque wire.

As noted, there are many variations of the disclosed concept which can be relied on to produce a catheter having these desirable characteristics. As noted, the stranding of the fibers can be undertaken with variations in pitches and directions in a single layer or in multiple layers. These parameters can also be varied in different axial sections of the same layer. The catheter, of course can be formed with or without the distal exit port 49 or the torque member 50. The central core member 61 can have a solid configuration, as in the case of an optical fiber, or a hollow configuration as in the case of the tube 73.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A fiberoptic catheter having an axis extending between a proximal end and an opposing distal end, the catheter comprising:
   a first plurality of optical fibers disposed in an ordered spiral configuration around the axis and arranged in a circumferential layer having a thickness equal to the diameter of one of the fibers with adjacent fibers in the layer having a contiguous relationship;
   the fibers being arranged to spiral in a first direction between the proximal end and the distal end of the catheter so that rotation of the catheter in the first direction tends to expand the circumferential layer while rotation of the catheter in a second direction opposite to the first direction tends to contract the circumferential layer;
   first means disposed outwardly of the circumferential layer for limiting the expansion of the circumferential layer when the catheter is rotated in the first direction;
   second means disposed inwardly of the circumferential layer for limiting the contraction of the circumferential layer when the catheter is rotated in the second direction;
   a second plurality of optical fibers included in the second means and arranged in a spiral configuration around the axis in a second circumferential layer, the second layers arranged to spiral in the second direction between the proximal end and the distal end of the catheter so that axial rotation of the catheter in the first direction tends to contract the second circumferential layer while axial rotation of the catheter in the second direction tends to expand the second circumferential layer;
   a third plurality of optical fibers included in the first means and arranged in a spiral configuration around the axis in a third circumferential layer;
   the third fibers being arranged to spiral in the second direction between the proximal end and the distal end of the catheter so that axial rotation of the catheter in the second direction contracts the third cylindrical layer while axial rotation of the catheter in the first direction expands the third cylindrical layer; whereby
   an interference fit exists between the first layer and the third layer when the catheter is rotated in the first direction, and between the first layer and the second layer when the catheter is rotated in the second direction.

2. The catheter recited in claim 1 wherein the first, second and third plurality of optical fibers include at least one fiber having a particular diameter and at least one other fiber having a diameter greater than the particular diameter.

3. The catheter recited in claim 2 wherein the one fiber and the one other fiber are disposed in different layers.

4. A fiberoptic catheter having an axis extending between a proximal end and an opposing distal end, the catheter comprising:
   a multiplicity of optical fibers arranged to spiral around the axis of the catheter in at least first, second, and third circumferential layers;
   the fibers in the first circumferential layer forming a first spiral having a first pitch;
   the fibers in the second circumferential layer forming a second spiral having a second pitch;
   the fibers in the third circumferential layer forming a third spiral having a third pitch; and
   at least one of the first pitch, second pitch and third pitch being different than the other two of the first, second, and third pitch.

5. The catheter recited in claim 4 wherein the first pitch and the third pitch are substantially equivalent.

6. The catheter recited in claim 4 wherein each of the first pitch, second pitch and third pitch is within a range of about 0.125 to 1.0 inches.

7. The catheter recited in claim 4 wherein each of the first pitch, second pitch and third pitch is within a range of about 0.2 to 0.8 inches.

8. The catheter recited in claim 4 wherein each of the optical fibers has a diameter in a range of about 30 microns to 200 microns.

9. The catheter recited in claim 8 wherein each of the optical fibers has a diameter in a range of about 50 microns to 80 microns.

10. A catheter having an axis extending between a proximal end and an opposing distal end, the catheter comprising:
    a plurality of optical fibers extending between the proximal end and the distal end of the catheter in an ordered arrangement wherein adjacent fibers in the arrangement have a contiguous relationship, the ordered arrangement including a plurality of first fibers disposed to spiral around the axis in a first direction and to form a first circumferential layer, and further including
    a plurality of second fibers disposed to spiral around the axis and the first fiber in a second direction to form a second circumferential layer outwardly of the first circumferential layer;

the catheter being bendable between a first position wherein the axis of the catheter is generally straight and the catheter in radial cross-section has a first shape, and a second position wherein the axis of the catheter forms a curve having an inner radius and an outer radius and the catheter in radial cross-section has a second shape along the curve;

at least one of the fibers extending from a first point in proximity to the outer radius of the curve, where the fiber has a tensile stress, and a second position in proximity to the inner radius of the curve, where the fiber has a compressive stress, so that the bending stresses in the fiber tend to equalize; whereby the second shape is maintained in a configuration substantially similar to the first shape.

11. The catheter recited in claim 10 wherein the arrangement includes a plurality of third fibers disposed to spiral around the axis, the first layer, and the second layer in the first direction to form a third circumferential layer outwardly of the second circumferential layer.

12. The catheter recited in claim 11 wherein at least one of the first, second and third fibers is an electrical fiber.

13. The catheter recited in claim 11 wherein at least one of the first, second and third fibers includes a radiopaque fiber.

14. A fiberoptic catheter having an axis extending between a proximal end and an opposing distal end, the catheter comprising:

a first axial section of the catheter;

a second axial section of the catheter disposed distally of the first axial section of the catheter;

a first plurality of optical fibers arranged contiguously in a spiral configuration to form a first circumferential layer extending in the first axial section and the second axial section around the axis of the catheter;

the first plurality of optical fibers in the first axial section having a first pitch;

the first plurality of optical fibers in the second axial section having a second pitch different from the first pitch;

a second plurality of optical fibers arranged contiguously in a spiral configuration to form a second cylindrical layer outwardly of the first cylindrical layer;

a third plurality of optical fibers arranged contiguously in a spiral configuration to form a third cylindrical layer outwardly of the second cylindrical layer;

the first plurality of fibers arranged to spiral in one of a clockwise and a counter-clockwise direction; and at least one of the second and third plurality of fibers arranged to spiral in the other of the clockwise and counter-clockwise direction.

15. The catheter recited in claim 14 wherein at least two of the fibers have a different diameter.

16. The catheter recited in claim 14 wherein at least two of the fibers spiral at a different pitch.

17. The catheter recited in claim 14 wherein at least two of the fibers spiral in different directions.

18. The catheter recited in claim 14 wherein the circumferential layers include at least one radiopaque fiber.

19. The catheter recited in claim 14 wherein the circumferential layers include at least one electrical fiber.

20. A laser catheter having an axis extending between a proximal end and an opposing distal end, the catheter comprising:

a longitudinal core extending along the catheter;

a multiplicity of optical fibers arranged around the core and having properties for conducting light between the proximal end and the distal end of the catheter;

a first plurality of the fibers spiraling around the core in one of a clockwise and counterclockwise direction and forming a first circumferential layer around the core; and a second plurality of the fibers spiraling around the core in the other of the clockwise and counterclockwise directions and forming a second circumferential layer outwardly of the first circumferential layer.

21. The laser catheter recited in claim 20 further comprising:

a third plurality of fibers spiraling around the core in the one direction and forming a third circumferential layer outwardly the first circumferential layer, second circumferential layer, and the core.

22. The laser catheter recited in claim 20 wherein the core is an optical fiber disposed along the axis of the catheter.

23. The laser catheter recited in claim 20 wherein the core is a tube forming an open channel along at least a portion of the axis of the catheter.

24. The laser catheter recited in claim 23 wherein:

portions of the tube define an exit port extending from the channel through the tube; and the exit port is spaced from the distal end of the catheter a distance which is not less than 25 centimeters.

25. The laser catheter recited in claim 24 wherein the exit port is spaced from the distal end of the catheter a distance which is in a range between 25 and 50 centimeters.

26. A method of making a catheter having an axis extending between a proximal end and an opposing distal end, the method comprising the steps of:

providing a first plurality of optical fibers each having properties for conducting light between the proximal end and the distal end of the catheter;

wrapping the fibers around the axis of the catheter to form a first cylindrical layer between the proximal end and the distal end of the catheter, the first layer having properties for expanding radially when the catheter is twisted in a first direction and properties for contracting radially when the catheter is twisted in a second direction opposite to the first direction;

providing a cylindrical outer surface inwardly of the first layer creating an interference fit with the contracting first layer when the catheter is twisted in the second direction;

providing a second optical fiber having a cylindrical outer surface disposed inwardly of the first layer and creating an interference fit with the contracting first layer when the catheter is twisted in the second direction; and providing a cylindrical inner surface outwardly of the fiber layer to create an interference fit with the expanding fiber layer when the catheter is twisted in the first direction.

27. The method recited in claim 26 wherein the first providing step includes the step of providing a plurality of fibers including at least one radiopaque fiber.

28. A method of making a catheter having an axis extending between a proximal end and an opposing distal end, the method comprising the steps of:

provide a first plurality of optical fibers each having properties for conducting light between the proximal end and the distal end of the catheter;

wrapping the fibers around the axis of the catheter to form a first cylindrical layer between the proximal end and the distal end of the catheter, the first layer having properties for expanding radially when the catheter is twisted in a first direction and properties for contracting radially when the catheter is twisted in a second direction opposite to the first direction;

providing a cylindrical outer surface inwardly of the first layer creating an interference fit with the contracting first layer when the catheter is twisted in the second direction;

providing a second plurality of optical fibers;

wrapping the second plurality of optical fibers around the first plurality of optical fibers to form a second cylindrical layer around the first cylindrical layer, the second circumferential layer providing a cylindrical inner surface outwardly of the first layer to create an interference fit with the expanding first layer when the catheter is twisted in the first direction.

29. The method recited in claim 28 wherein the first wrapping step includes the step of spiraling the first optical fibers around the axis of the catheter to form the single cylindrical layer; and the second wrapping step includes the step of spiraling the second optical fibers around the first optical fibers to form the second cylindrical layer.

30. A method of making a catheter having an axis extending between a proximal end and an opposing distal end, the method comprising the steps of:

providing a plurality of optical fibers each having properties for conducting light between the proximal end and the distal end of the catheter, the plurality of optical fibers including at least a pair of optical fibers having different diameters;

wrapping the fibers around the axis of the catheter to form a single generally cylindrical layer between the proximal end and the distal end of the catheter, the layer having properties for expanding radially when the catheter is twisted in a first direction and properties for contracting radially when the catheter is twisted in a second direction opposite to the first direction;

providing a cylindrical outer surface inwardly of the fiber layer creating an interference fit with the contracting fiber layer when the catheter is twisted in the second direction;

providing a cylindrical inner surface outwardly of the fiber layer to create an interference fit With the expanding fiber layer when the catheter is twisted in the first direction.

31. A method of making a catheter having an axis extending between a proximal and an opposing distal end, the method comprising the steps of:

spiraling at least a first, second and third fibers around the axis to form a respective inner layer, a middle layer disposed outwardly of the inner layer, and an outer layer disposed outwardly of the middle layer;

torquing the catheter in a first axial direction to expand the middle layer radially outwardly and contract the outer layer radially inwardly to form an interference fit between the middle layer and the outer layer; and torquing the catheter in a second axial direction opposite to the first axial direction to contract the middle layer radially inwardly and expand the inner layer radially outwardly to form an interference fit between the middle .layer and the inner layer of the catheter.

32. The method recited in claim 31 wherein the spiraling step includes the step of spiraling the second fiber in a direction opposite to at least one of the first fiber and the third fiber.

33. The method recited in claim 31 wherein the spiraling step comprises the step of spiraling the second fiber at a pitch different than the pitch of one of first fiber and the third fiber.

34. The method recited in claim 31 wherein at least one of the first, second and third fibers is spiraled at a variable pitch in its respective layer.

35. The method recited in claim 31 further comprising the step of forming a jacket around the fibers.

36. The method recited in claim 35 wherein the forming step includes the step of extruding a jacket around the fibers between the proximal end and the distal end of the catheter.

37. A laser catheter having an axis extending between a proximal end and an opposing distal end, the catheter comprising:

a longitudinal core extending along the catheter;

a multiplicity of optical fibers arranged around the core and having properties for conducting light between the proximal end and the distal end of the catheter;

a circumferential layer of the fibers disposed around the core and having properties for expanding circumferentially when the catheter is torqued in a first direction and properties for contracting circumferentially when the catheter is torqued in a second direction opposite to the first direction;

means for limiting the expansion of the layer of fibers when the catheter is torqued in the first direction and for limiting the contraction of the layer of fibers when the catheter is torqued in the second direction;

first means included in the limiting means for limiting the expansion of the layer, the first means including a second layer of fibers disposed circumferentially outwardly of the first layer and having properties for contracting circumferentially when the catheter is torqued in the first direction; and second means included in the limiting means and disposed inwardly of the layer of fibers to limit the contraction of the layer when the catheter is torqued in the second direction.

38. A laser catheter having an axis extending between a proximal end and an opposing distal end, the catheter comprising:

a longitudinal core extending along the catheter;

a multiplicity of optical fibers arranged around the core and having properties for conducting light between the proximal end and the distal end of the catheter;

a circumferential layer of the fibers disposed around the core and having properties for expanding circumferentially when the catheter is torqued in a first direction and properties for contracting circumferentially when the catheter is torqued in a second direction opposite to the first direction;

means for limiting the expansion of the layer of fibers when the catheter is torqued in the first direction and for limiting the contraction of the layer of fibers when the catheter is torqued in the second direction;

first means included in the limiting means and disposed outwardly of the layer of fibers for limiting the expansion of the layer when the catheter is torqued in the first direction; and second means included in the limiting means for limiting the contraction of the layer when the catheter is tourqued in the second direction, the second means including a second layer of the fibers disposed circumferentially inwardly of the first layer and having properties for expanding circumferentially when the catheter is torqued in the second direction.

39. A laser catheter having an axis extending between a proximal end and a distal end of the catheter, comprising:

a first axial section of the catheter;

a second axial section of the catheter disposed proximally of the first axial section of the catheter;

a tube defining a lumen along the axis of at least the first axial section;

first portions of the tube disposed in the first axial section and second portions of the tube disposed in the second axial section;

torque means disposed in the lumen of the second portion of the tube for rotating the catheter along the axis of the catheter;

a multiplicity of optical fibers extending through the first axially section and the second axial section;

the fibers in the first axial section forming a first spiral having a first pitch; and the fibers in the second axial section forming a second spiral having a second pitch longer than the first pitch.

40. A laser catheter having an axis extending between a proximal end and a distal end of the catheter, comprising:

a first axial section of the catheter;

a second axial section of the catheter disposed proximally of the first axial section of the catheter;

a third axial section of the catheter disposed proximally of the second axial section;

a multiplicity of optical fibers extending through the first axial section, the second axial section, and the third axial section;

the fibers in the first axial .Section forming a first spiral having a first pitch;

the fibers of the second axial section forming a second spiral having a second pitch longer than the first pitch; and the fibers in the third axial section extending in a generally parallel relationship with the axis of the catheter.

41. A laser catheter having an axis extending between a proximal end and a distal ehd of the catheter, comprising:

a first axial section of the catheter;

a second axial section of the catheter disposed proximally of the first axial section of the catheter;

a first plurality of optical fibers forming a first spiral and one of a clockwise and counter-clockwise direction around the axis;

a second plurality of optical fibers forming a second spiral in the other of the clockwise and counter-clockwise direction around the axis of the catheter;

at least the first plurality of fibers extending through the first axial section and the second axial section of the catheter;

the first plurality of fibers in the first axial section forming a first spiral having a first pitch; and the first plurality of optical fibers in the second axial section forming a second spiral having a second pitch longer than the first pitch.

42. A laser catheter system, comprising:

a laser;

a catheter coupled to the lasers and having an axis extending between a proximal end and an opposing distal end;

a core included in the catheter and having a generally cylindrical outer surface;

a multiplicity of optical fibers having properties for conducting light between the proximal end and the distal end of the catheter, the fibers being enclosed in an ordered arrangement along substantially the entire distance between the proximal end and the distal end, with each of the fibers having a non-parallel relationship with the axis of the catheter;

a first layer of the optical fibers surrounding the core;

a second layer of the optical fibers surrounding the first layer of optical fibers;

a first optical fiber included in the first layer and having a first bending path around the core;

a second optical fiber included in the first layer and having a second bending path around the core; and the first bending path having substantially the same length as the second bending path.

* * * * *